United States Patent [19]
Carlson et al.

[11] Patent Number: 5,792,195
[45] Date of Patent: Aug. 11, 1998

[54] ACCELERATION SENSED SAFE UPPER RATE ENVELOPE FOR CALCULATING THE HEMODYNAMIC UPPER RATE LIMIT FOR A RATE ADAPTIVE CARDIAC RHYTHM MANAGEMENT DEVICE

[75] Inventors: Gerrard M. Carlson, Champlin; Bruce R. Jones, Hopkins; Julio C. Spinelli, Shoreview, all of Minn.

[73] Assignee: Cardiac Pacemakers, Inc., St. Paul, Minn.

[21] Appl. No.: 766,339

[22] Filed: Dec. 16, 1996

[51] Int. Cl.⁶ .............................. A61N 1/36; A61N 1/365
[52] U.S. Cl. .................................. 607/17; 607/18; 607/19
[58] Field of Search ......................... 607/17–19; 128/701, 128/714, 715

[56] References Cited

U.S. PATENT DOCUMENTS

| | | |
|---|---|---|
| 4,428,380 | 1/1984 | Wong et al. ........................ 128/715 |
| 4,446,872 | 5/1984 | Marsoner et al. .................. 128/715 |
| 4,649,930 | 3/1987 | Groch et al. ....................... 128/715 |
| 4,763,646 | 8/1988 | Lekholm . | 
| 5,109,863 | 5/1992 | Semmlow et al. ................. 128/715 |
| 5,156,147 | 10/1992 | Warren et al. . |
| 5,179,947 | 1/1993 | Meyerson et al. . |
| 5,235,976 | 8/1993 | Spinelli . |
| 5,554,177 | 9/1996 | Kieval et al. ...................... 607/17 |
| 5,609,613 | 3/1997 | Woodson et al. . |
| 5,626,622 | 5/1997 | Cooper ............................... 607/18 |

FOREIGN PATENT DOCUMENTS 361517  4/1990  WIPO .

OTHER PUBLICATIONS

"Cardiac Auscultation: The First and Second Heart Sounds" by Jame A. Ronan, Jr., Heart Disease and Stroke, May/Jun. 1992, pp. 113–116.

*Primary Examiner*—William E. Kamm
*Assistant Examiner*—Carl H. Layno
*Attorney, Agent, or Firm*—Haugen and Nikolai, P.A.

[57] ABSTRACT

An implantable cardiac rhythm management device includes an accelerometer along with apparatus for processing the analog signal output from the accelerometer for deriving therefrom the time of occurrence of a selected heart sound in relation to a previously occurring ventricular depolarization event. The thus-derived heart sound information can be used to establish a hemodynamic upper rate limit for a rate adaptive pacemaker.

20 Claims, 8 Drawing Sheets

ACCELERATION SENSED SAFE UPPER RATE ENVELOPE FOR CALCULATING THE HEMODYNAMIC UPPER RATE LIMIT FOR A RATE ADAPTIVE CARDIAC RHYTHM MANAGEMENT DEVICE

BACKGROUND OF THE INVENTION

I. Field of the Invention

This invention relates generally to the field of signal processing, and more particularly to an apparatus and method for processing a signal stream from an accelerometer type sensor contained in a body-implantable, medical device, such as a cardiac pacemaker.

II. Discussion of the Prior Art

The Meyerson et al. U.S. Pat. No. 5,179,947 describes a rate adaptive cardiac pacemaker that utilizes an accelerometer housed in the pacemaker's can that is implanted in a patient's body for sensing the level of activity of the patient and producing a stimulation rate control signal proportional to the sensed activity level.

As is known in the art, in the case of rate adaptive pacemakers, it has been common practice to incorporate a programmed upper rate limit (URL) beyond which the pacemaker will not stimulate, even though the physiologic sensor employed may still be calling for an increase in pacing rate. The Warren et al. U.S. Pat. No. 5,156,157 describes a pacemaker that, instead of having a programmed URL, includes a further hemodynamic sensor to set the URL at a safe value that tends to limit the pacer's stimulation rate to a value where hemodynamic performance of the heart as a pump is optimized.

The Spinelli U.S. Pat. No. 5,235,976 teaches that the heart's "Active Time" can be used as a hemodynamic sensor in a pacer of the type described in the aforereferenced Warren et al. patent where "Active Time" is defined as the time elapsing between the occurrence of a paced or sensed ventricular depolarization signal and the end of the filling phase of the ventricles when the ventricles are being filled at their "fast-filling rate". The Spinelli patent teaches that Active Time can be derived from an impedance vs. time signal obtained using impedance plethysmography.

FIG. 1 depicts the events of a cardiac cycle showing changes in left atrial pressure, left ventricular pressure, aortic pressure, ventricular volume, the electrocardiogram and the phonocardiogram, the latter identifying the heart sounds $S_1$, $S_2$ and $S_3$. It is known that the time between the occurrence of a QRS complex and the $S_3$ heart sound associated with the flow of blood into the ventricles during diastole, closely approximates the heart's Active Time. Thus, if it were possible to accurately determine from an accelerometer signal disposed in an implanted pacer the time of occurrence of the heart sound $S_3$, the same accelerometer used to sense physiologic activity could also be used as the hemodynamic sensor in establishing a hemodynamically determined URL for a rate adaptive pacemaker. The $S_3$ heart sound is relatively weak and in a noisy environment is quite difficult to discern. Heart sounds $S_1$, and $S_2$, however, are relatively robust and we have devised a signal processing approach for extracting the $S_2$ heart sound from an accelerometer output even in the presence of noise due to body movement or the like. By determining the $S_2$ to $S_3$ interval when the patient is at rest (the noise level is low) and treating that interval as a constant when the patient is up and about, the QRS to $S_3$ interval, i.e., the heart's Active Time can then be computed as:

$$AT = QRS\ to\ S_3 = (QRS\ to\ S_2)_{active} + (S_2\ to\ S_3)_{rest}$$

It is accordingly the principal object of the present invention to provide a signal processing system capable of receiving as an input a signal train emanating from an accelerometer implanted in the body of a patient and providing as an output a value equal to the time interval between an immediately preceding R-wave and the following $S_2$ heart sound.

SUMMARY OF THE INVENTION

The foregoing features, objects and advantages of the invention are achieved by incorporating into an implantable cardiac pacemaker a signal processing circuit for recovering heart sounds from an implanted accelerometer that produces and electrical, time-varying output signal related to vibrational forces present within the body. This time varying output signal is band-pass filtered such that the resulting output from the filter stage is a signal train whose frequency components fall within a predetermined range frequencies characteristic of heart sounds and in which amplified noise components are discriminated against. This filtered output signal is next applied to an automatic gain control circuit which functions to limit the extent of excursions of the filtered output signal emanating from the bandpass filter from a predetermined baseline to thereby suppress large amplitude, short-term transient noise spikes. Next, an analog envelope of the accelerometer signal is determined by low pass filtering the absolute value of the analog output from the AGC stage. That envelope signal is then logarhythmically compressed to yield an output voltage measured in decibels. This output voltage may then be subjected to analog-to-digital conversion in which the processed accelerometer signal is digitized to a predetermined word size, e.g., eight bits, and at a predetermined sampling rate, e.g. 500 Hz. The digitized accelerometer signal envelope is then processed in accordance with further signal processing algorithms in a microprocessor in a way to extract a heart sound value in a time windowed interval for each beat of successive cardiac cycles. Specifically, a window having a starting time and ending time relative to a preceding R-wave detection and varying with heart rate is defined by empirically determined equations based upon analysis of cardiac data from a relatively large patient population so as to bracket a predetermined heart sound, e.g., $S_2$.

The heart sound information bracketed by the window is then ensemble averaged over a number of beats and the results thereof are treated as a signal that is next smoothed and subjected to further signal processing operations so as to locate the peak of the heart sound signal of interest in terms of a time interval from the occurrence of a preceding R-wave.

DESCRIPTION OF THE DRAWINGS

Various features, objects and advantages of the invention will become apparent to those skilled in the art from the following detailed description of a preferred embodiment of the invention, especially when considered in conjunction with the accompanying drawings in which.

Figure 1:
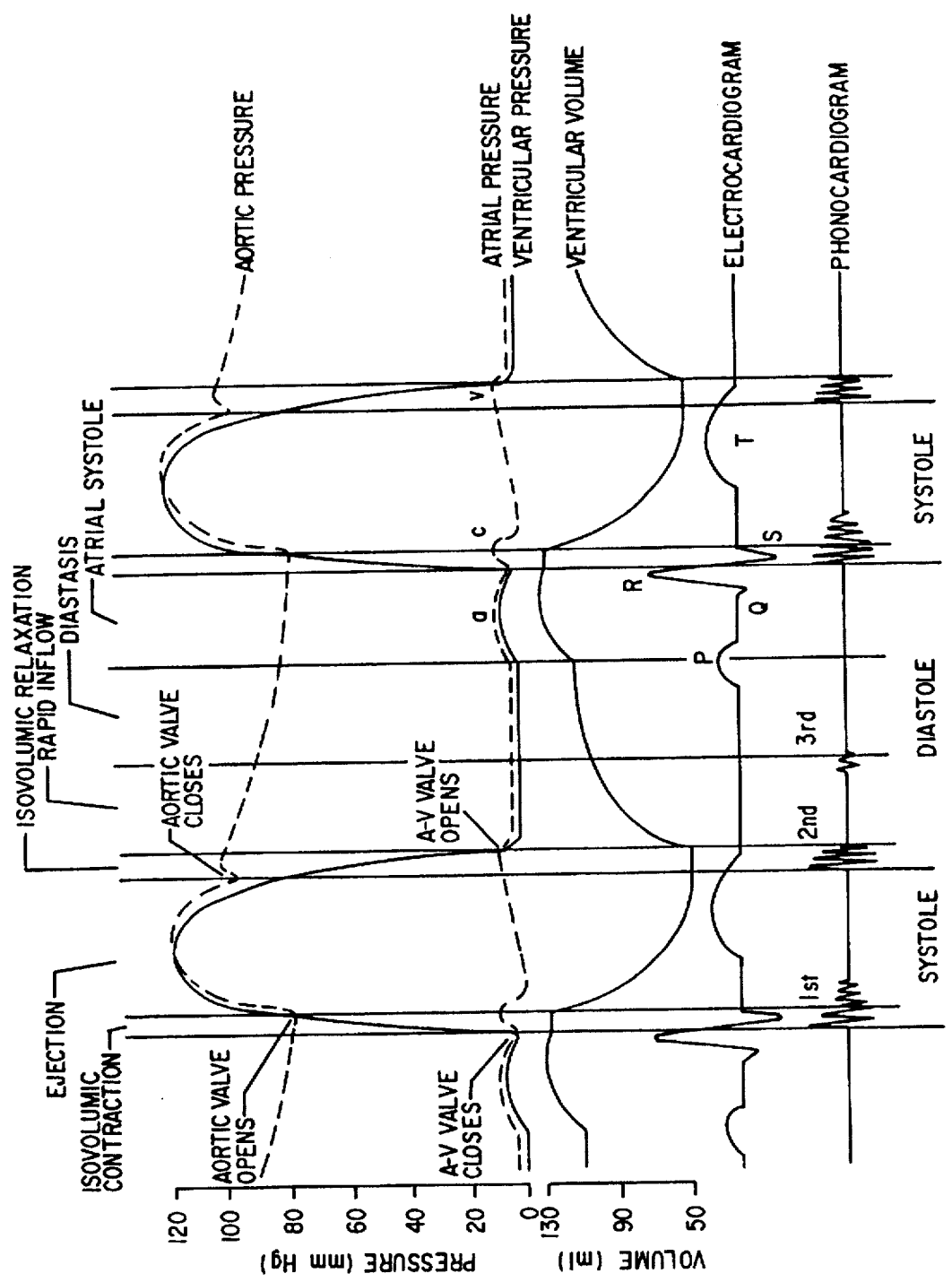
FIG. 1 is a plot of the events of the cardiac cycle, showing changing in left arterial pressure, left ventricular pressure, aortic pressure, ventricular volume, the electrogram, and the phonocardiogram taken from page 102 of the Text Book of Medical Physiology, Eighth Edition by Guyton, copyright 1991.
Figure 3A:
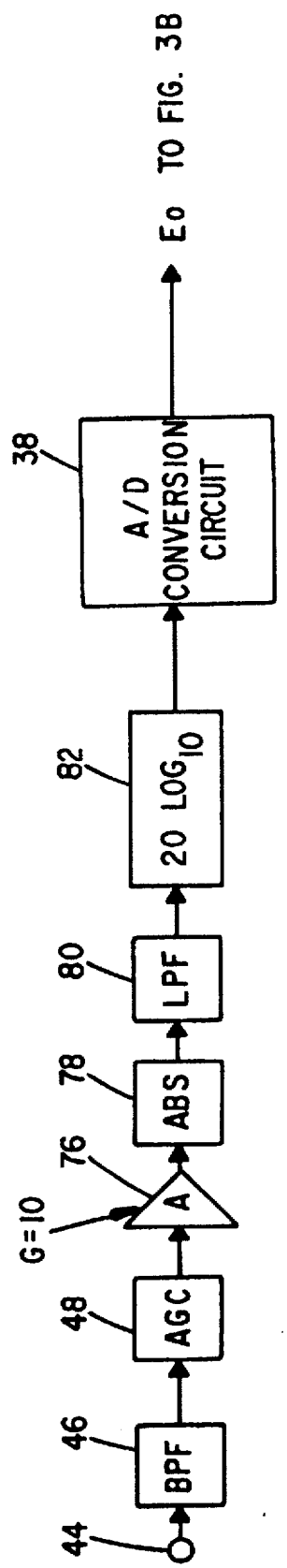
FIGS. 3A through 3C when arranged as shown in FIG. 3 is a schematic diagram of the signal processing steps
Figure 4:
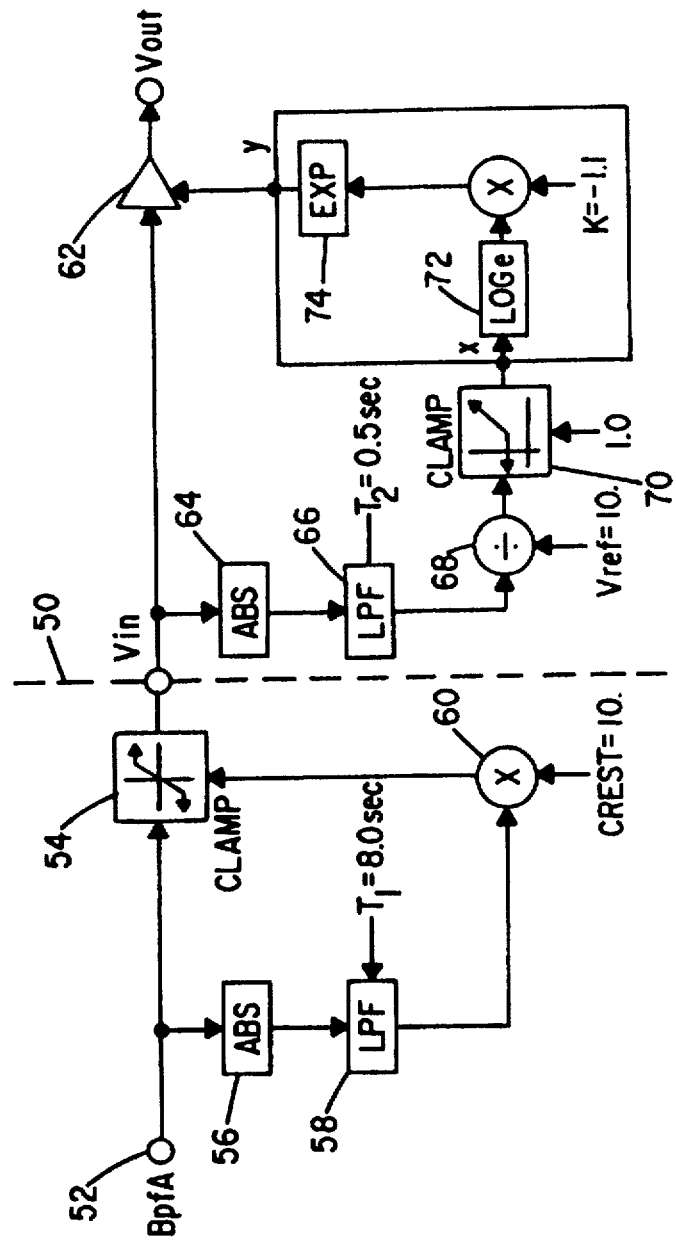
Figure 5:
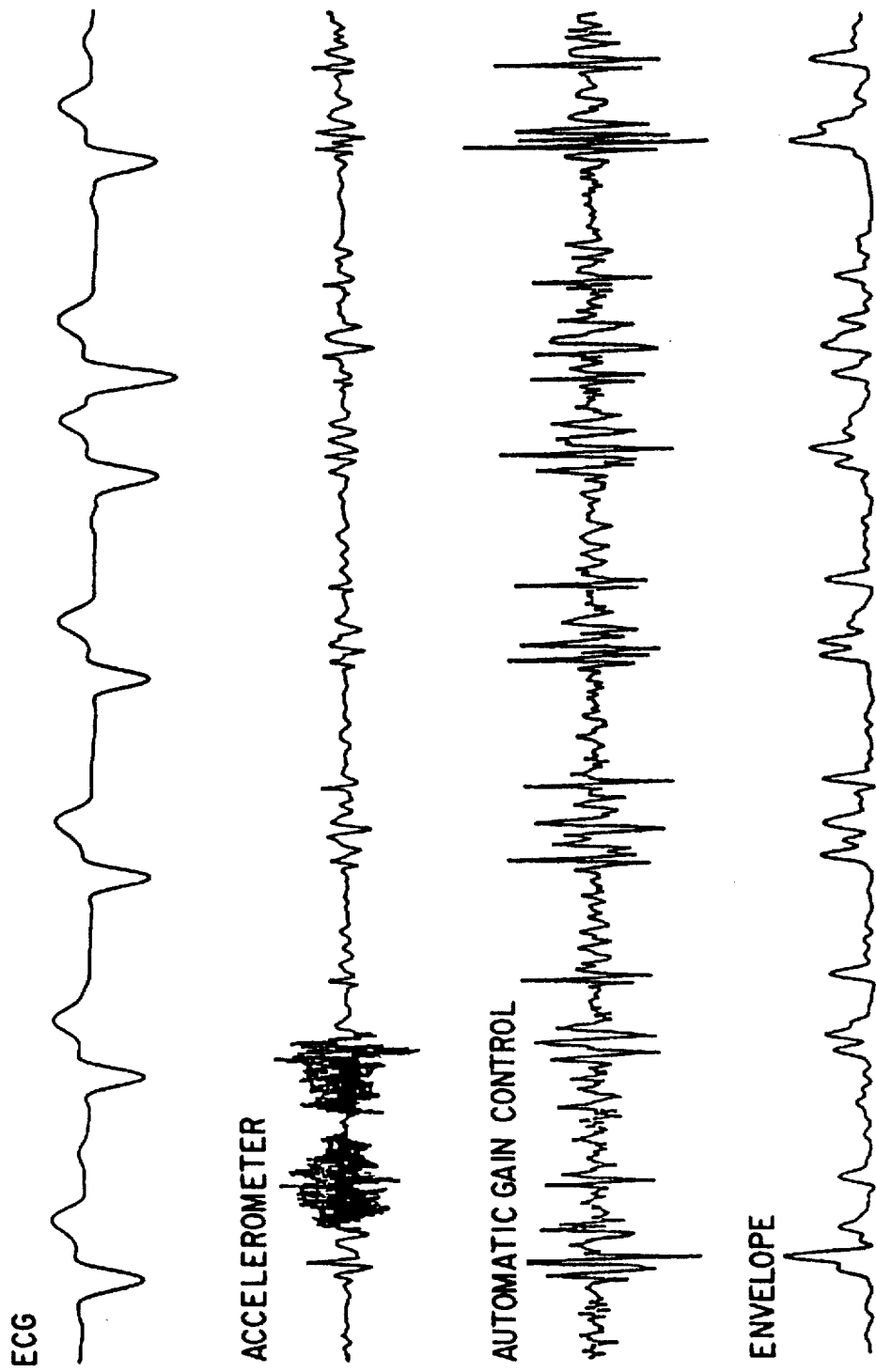
Figure 6:
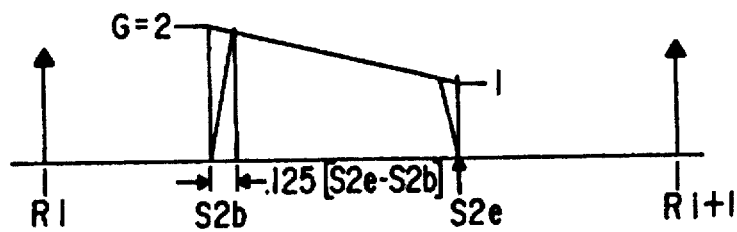
Figure 7:
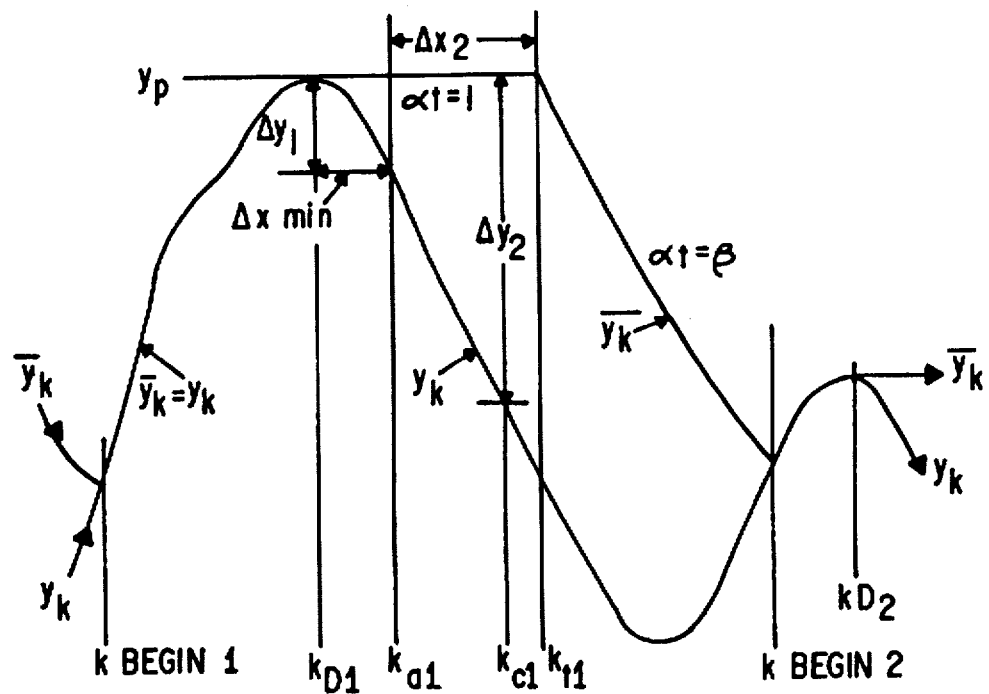

3 employed in locating the time of occurrence of the second heart sound shown in the phonocardiogram waveform of FIG. 1;

FIG. 4 is a schematic diagram of the AGC circuit of FIG. 3a;

FIG. 5 illustrate representative waveforms of an ECG signal that is aligned timewise with a raw accelerometer output signal, the output of the AGC operation and the analog waveform envelope derived from low pass filtering of the absolute value of an amplified version of the output from the AGC operation;

FIG. 6 illustrates a time window of the accelerometer signal envelope that is extracted for each beat of a cardiac cycle for isolating heart sound $S_2$; and FIG. 7 is a plot helpful in understanding the peak detect function for the ensemble averaged waveform.

DESCRIPTION OF THE PREFERRED EMBODIMENT

Referring to FIG. 1, there is reproduced a plot showing the significant events in a cardiac cycle taken from the Text Book of Medical Physiology, Eighth Edition by Guyton, showing variations in left arterial and left ventricular pressure, aortic pressure and ventricular volume in time alignment with an electrocardiogram waveform and a phonocardiogram. Of particular interest in connection with the present invention are the first, second and third heart sounds comprising the phonocardiogram. The first heart sound is associated with the closure of the A–V valve in the heart and the opening of the aortic valve. Similarly, heart sound $S_2$ is associated with the subsequent closure of the aortic valve. Heart sound $S_3$ is associated with the end of the fast-filling phase of the heart during diastole.

As can be seen from FIG. 1, heart sounds $S_1$ and $S_2$ have relatively large amplitude excursions as compared to the heart sound $S_3$. As is mentioned in the introductory portion of this application, in establishing a hemodynamic upper rate limit for a rate responsive pacemaker, one may wish to determine the active time of the heart and that the active time is closely approached by the interval beginning with a R-wave and ending with the occurrence of the third heart sound, $S_3$.

While phonocardiogram equipment can be used to locate $S_3$, that equipment is not suitable for implantation as a part of a cardiac rhythm management device due to its size, complexity and power requirements. An accelerometer is readily implantable. However, the signal component due to $S_3$ is difficult, if not impossible, to directly isolate from the raw accelerometer signal. This is due primarily to the level of noise present in the raw signal emanating from the accelerometer transducer which is preferably incorporated into the implantable housing containing the circuitry implementing the cardiac rhythm management device. Thus, to be effective in establishing an upper rate limit for a rate adaptive pacemaker, a means must be provided for accurately establishing the length of the interval between the occurrence of a ventricular depolarization signal (R-wave) and the occurrence of the next following $S_3$. By making the assumption that the interval between $S_2$ and $S_3$ does not vary with heart rate, a measurement may be taken with the patient at rest to determine the $S_2$ to $S_3$ interval and then adding that measured interval to the interval from the occurrence of an R-wave to the resulting $S_2$ heart sound. There will now be described the features of an implantable cardiac pacemaker that incorporates unique signal processing apparatus for accurately measuring the R-wave to $S_2$ heart sound when the patient in whom the device is implanted is in an active, non-resting state.

Figure 2:
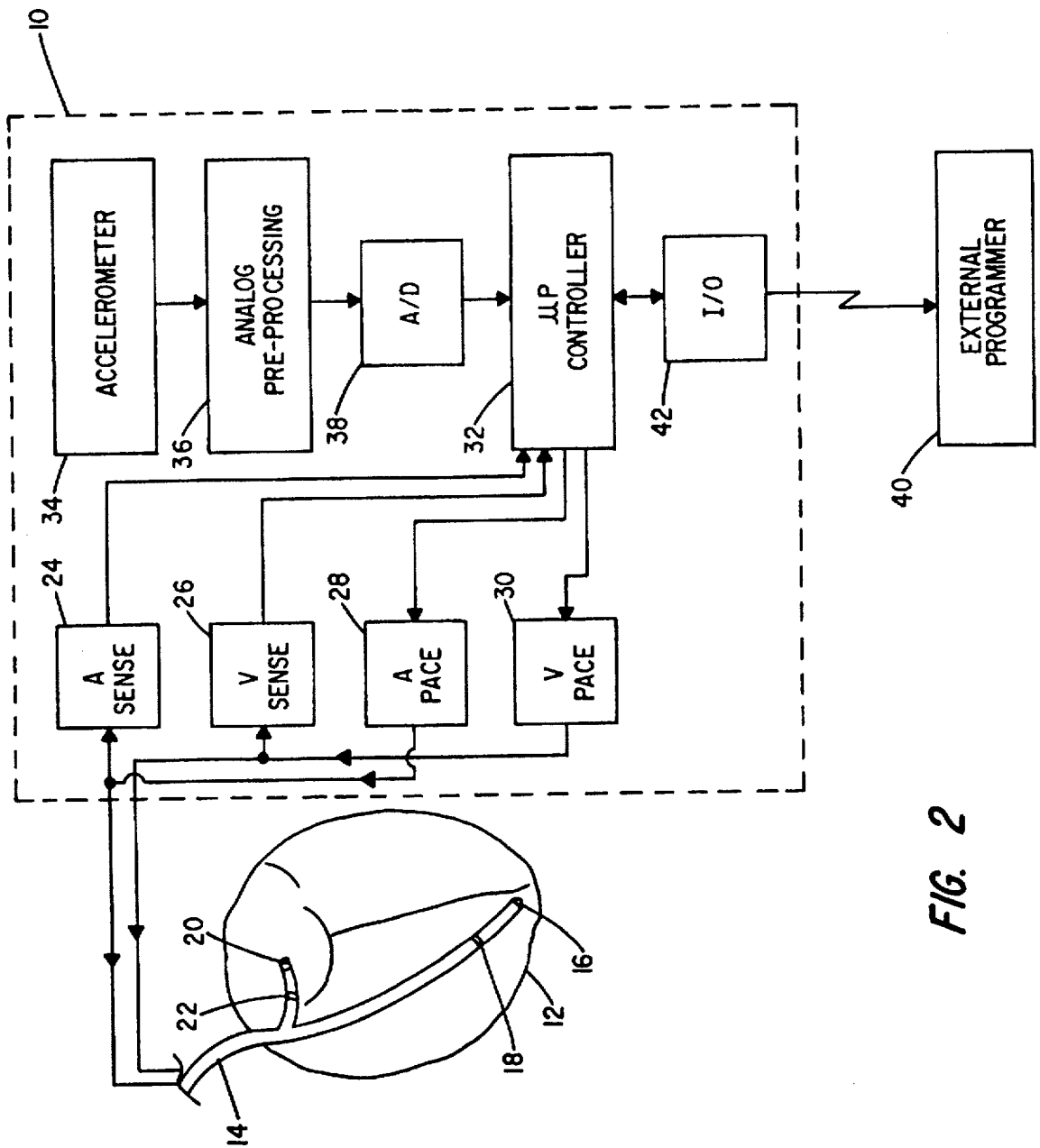
FIG. 2 is a schematic block diagram of an implantable rate-adaptive pacer in accordance with the present invention.

Referring to FIG. 2, there is illustrated a rate adaptive, dual-chamber cardiac pacemaker whose pacing rate is controlled as a function of activity with activity being sensed by an implanted accelerometer. The implantable device is shown as being enclosed by broken line box 10 and is operatively coupled to the patient's heart 12 by means of a conventional pacing lead 14. The lead 14 has a stimulating tip electrode 16 adapted to be disposed in the right ventricle and associated with it is a bipolar sensing electrode 18 in the form of a conductive ring disposed on the insulating sheath of the lead. Being a dual-chamber pacemaker, the lead 14 also includes an atrial stimulating electrode 20 and an atrial sensing electrode 22, each being disposed in the right atrial chamber of the heart.

The implantable device 10 includes an atrial sense amplifier 24, a ventricular sense amplifier 26, an atrial stimulating circuit 28 and a ventricular stimulating circuit 30. Sensed atrial and ventricular depolarization signals are applied to the respective sense amplifiers 24 and 26 with the resulting outputs being fed to a microprocessor-based controller 32. Controller 32 is programmed to process the received signals and provides control signals to the atrial pulse generator 28 and the ventricular pulse generator 30 for providing stimulating pulses to the heart via electrodes 16 and 20 at appropriate times. Also providing an input to the microprocessor controller is an accelerometer 34 whose analog output is band-pass filtered, AGC limited and otherwise processed in the analog preprocessing circuitry 36 before being converted to a digital form by A/D converter 38. Provision may also be made for bidirectional communication between the implanted device 10 and an external programmer 40 by way of input/output circuit 42.

As will be explained in greater detail, the V-sense signal from sense amplifier 26 is utilized by the microprocessor-based controller 32 along with the preprocessed and digitized signals from the accelerometer 34 to perform further signal processing steps in arriving at the $S_2$ interval. The $S_2$ interval is then added to the previously determined interval from $S_2$ to $S_3$ measured while the patient is at rest to arrive at the $S_3$ interval with the patient active such that the upper rate limit for the rate adaptive pacemaker 10 can be computed and used to establish a hemodynamic upper rate limit.

The present invention primarily centers upon the signal processing apparatus and algorithms for reliably deriving the $S_2$ interval from the raw accelerometer signals when the patient is actively engaged in normal day-to-day activities. It can be appreciated that the accelerometer output includes not only signal components due to various events in the cardiac cycle but also body motion artifacts and other sources of noise. It is the function of the signal processing circuitry incorporated into the device 10 to reliably segregate and isolate the time of occurrence of the peak of the second heart sound, even in the presence of such noise. While the invention will be described in connection with finding the second heart sound, those skilled in the art reading the specification will appreciate that by selecting alternate filter constants and other parameters associated with the signal processing algorithms, it is possible to isolate and focus on heart sound $S_1$ as well.

Referring to FIG. 3A of the drawings, there is schematically illustrated the circuitry implementing the analog preprocessing block 36 in FIG. 2. The raw analog signal output from the accelerometer 34 is applied at terminal 44 which is an input to a bandpass filter 46. The upper and lower cutoff frequencies, when focusing on heart sound $S_2$, have been determined by empirical analysis of accelerometer data taken from a large number of patients. Specifically, with a lower cutoff frequency of about 23 Hz and an upper cutoff frequency of about 45 Hz, it has been found that the bandwidth of such a filter tends to minimize the amount of noise due to breathing, body motion, muscle twitch, speech, amplifier noise, etc., without distorting the shape of the $S_2$ heart sound.

The output from the bandpass filter 46 feeds into an automatic gain control (AGC) circuit 48 which is configured to provide an output corresponding to the RMS level of the input thereto. FIG. 4 is a schematic diagram of the AGC circuit 48 and it is divided into two functional parts by the vertical dotted line 50. The circuitry to the left of the dotted line 50 is designed to prevent the circuitry to the right thereof from being unduly modified by short-term transient noise spikes that happen to get through the bandpass filter 46. The terminal 52, labeled "BpfA", is connected to the output of the bandpass filter 46 and connects to a clamp circuit 54 whose bias is provided, via absolute value circuit 56, low pass filter 58, and an amplifier 60. By providing the low pass filter 58 with a time constant of about 8 seconds and the amplifier 60 with an amplification factor of about 10, the clamping circuit 54 is effective to limit its output signal to a value approximately equal to the RMS value of the bandpass filtered accelerometer signal, even in the presence of short-term transient noise signals that far exceed 10 times the RMS value.

The portion of the AGC circuit to the right of the vertical-dashed line 50 controls the gain of an amplifier 62. Again, the output from the clamp circuit 54 is applied through an absolute value circuit 64 and a low pass filter circuit 66 to an attenuating circuit 68 controlling the bias of a clamp circuit 70. The low pass filter 66 may preferably have a time constant of about 0.5 seconds, considerably shorter than the time constant of the low pass filter 58. The 0.5 second time constant of low pass filter 66 is appropriate for processing heart sound signals. By providing the attenuation circuit 68 in combination with the clamp circuit 70, it is possible to use the output of lowpass circuit 66 as an rms level dependent signal gain control. When the output of lowpass circuit 66 exceeds 10, the output of clamp 70 exceeds 1. When the output of block 66 falls below 10, the output of clamp 70 remains at 1. This has the effect of limiting the gain adjustments to that of compression, where the compression threshold is function of Vref=10. With a unity input, the output of log circuit 72 will be a zero voltage causing the input to the exponential operator 74 to also be a zero whereby the signal output therefrom to be unity. However, if the input to the clamp circuit 70 (x) is greater than one, the log circuit 72 will output a voltage signs "$\log_e(x)$" that is multiplied by a constant "k- -1.1" that is selected 50 as to yield "$y=\exp[-1.1 \log_e(x)]$" at the output of exponential amplifier 74. For example, if "Vin" causes an output of 10 (or less) to be produced at the output of lowpass filter 66, the output of clamp 70 will be 1 which results in an output from the exponential amplifier block 74 equaling "$y=\exp[-1.1 \log_e(1)]=1$". Again, if "Vin" causes the output of block 66 to become 100 or ten times that of the previous data, then the output "y" will become "$y=\exp[-1.1 \log_e(100/10)]=(1/12.6)$". Similarly, if "Vin" causes block 66 to yield 1000, the output "y" becomes "$y=[1.1\log_e(1000/10)]=1/158.5$". Summarizing, an increase of 10:1 from the reference "Vref" attenuation of 1/12.6, while another increase to 100 would yield an attenuation 1/158. This results in slight overcompression which is rarely noticed since abrupt rms level changes rarely exceed 10:1. However, this overcompression can be quite beneficial when sharp and quick increases in rms voltage, e.g., exceeding 10:1, are observed, since the data that follows is usually not useful and is short lived. This also serves to attenuate what the clamp circuit failed to edit out.

The gain of amplifier 62 is set to give the most likely occurring accelerometer data unity gain as seen from BpfA to Vout in FIG. 4. For this implementation, $S_2$ related cardiac accelerations were found to deliver an rms value of about 80 units at the output of lowpass filter block 66 most of the time. Therefore, in order to insure unity gain from BpfA to Vout, amplifier 62 needs to be set at $1/\exp[-1.1 \log_e(80/10)]$ or roughly 10.

The waveforms shown in FIG. 5 are somewhat typical, with the waveform labeled ECG representing that obtained from an electrocardiograph. Timewise aligned with it is a typical accelerometer output signal as it is applied to the input of the bandpass filter 46. The waveform labeled "automatic gain control" is illustrative of the same signal after undergoing preprocessing in the AGC circuit 48.

Referring again to FIG. 3A, the output from the AGC circuit 48 is amplified by an amplifier 76 having a gain of 10 which constitutes a scaled, normalized, filtered accelerometer signal. It is applied to an absolute value circuit 78 and then low pass filtered at 80 to thereby provide at the output of the filter the signal labeled "Envelope" in FIG. 5. It may be considered as a preconditioned heart sound envelope for $S_2$. The low pass filter circuit 80 preferably has a cut-off frequency of about 10 Hz.

Before being converted to a digital value by A/D converter 38 (FIGS. 2 and 3), it has proved expedient to first logarhymically compress the envelope signal by means of a 20 $LOG_{10}$ circuit 82. Thus, the output signal, $E_0$, is a log normalized heart sound envelope. By performing logarithmic compression, the $S_2$ envelope signal has a very consistent level allowing an 8-bit A/D conversion circuit 38 to be used.

Figure 3B:
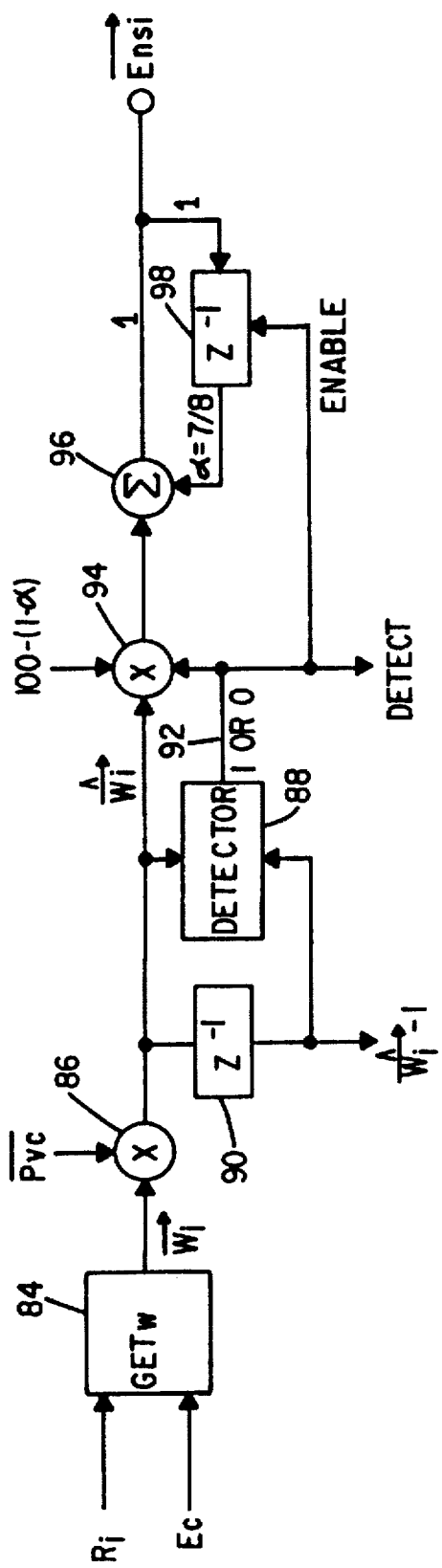

Referring next to FIG. 3B, there is illustrated a signal processing diagram helpful in understanding the operations performed in the microprocessor-based controller 32 for deriving the $S_2$ heart sound interval from the digitized values of $E_0$ as previously defined. Generally speaking, the processing steps represented by FIG. 3b are intended to take the digitized log normalized heart sound envelope $E_0$ and produce a vector comprising a list of numbers that basically characterize the value of $S_2$ heart sound envelope in a defined time interval which is determined by the operation labeled $GET_w$ (box 84). This operation receives an "R-wave" timing reference $R_1$ along with the digitized $E_0$ values at a 500 Hz sampling rate at which the A/D converter 38 may be designed to operate. The operator $GET_w$ functions to extract a time window of the digitized accelerometer signal envelope for each cardiac cycle. The i subscript functions as a beat index so that the symbol $R_i$ refers to the $i^{th}$ beat in a long series of such beats. Referring to FIG. 6, the windowing rules for effectively encompassing heart sound $S_2$ have been empirically determined and are based upon regression lines published in the Geigy Scientific Tables #5 (Heart and Circulation) ©1990 CIBA GEIGY Limited, Basal, Switzerland, page 124, Table 1 and is defined by a beginning point $S_{2b}$ and an ending point $S_{2e}$. The windowing rules are R-to-R interval dependent. At low heart rates, the search interval between $S_{2b}$ and $S_{2e}$ is wider than it is at high heart rates. The beginning and end points are set so as to straddle the expected time of $S_2$, based upon knowledge of the next expected R-to-R interval. The windowing rules are given below in counts at 500 Hz sample rate rather than in milliseconds.

| | |
|---|---|
| $S_{2b}$ = 119.0–.62500 | (HR – 120.0) for all HR |
| 198.0–2.0875 | (HR – 120.0) where HR < 120.0 bpm |
| $S_{2a}$ = 198.0–1.2250 | (HR – 120.9) where HR > 120.0 bpm |

Only those signal components in the $E_0$ signal falling between the beginning point and the end point of the window shown in FIG. 6 are included in subsequent computations in determining the $S_2$ interval.

The output from the $GET_w$ block 84 is represented by the symbol $W_i$ and is a vector of digitized heart sound envelope signals. To eliminate the effects of ectopic beats, the vector is multiplied by one if a normal beat is involved and by a zero if a premature ventricular contraction (PVC) is involved. This information, that is whether the beat is ectopic or not, is decided in the usual way by conventional pacemaker/circuitry. Thus "PVC" is readily available from existing technology. Thus, only heart sounds associated with normal sinus rhythm will be passed on to the valid beat detector circuit 88. Detection of valid $S_2$ beats is required to avoid averaging stray beats into an ensemble averaging operation which is yet to be described.

The strategy employed to determine beat validity is to compare a present and a previous windowed heart sound envelope. If the total error squared between adjacent heart sound envelope buffers is less than a threshold times the variance of either heart sound envelope, then the current beat is declared valid. The previous beat vector is derived using a one unit beat delay element 90 to yield a vector $W_{i-1}$ and is fed to one input of the detector 88. The other input to the detector is the current beat vector $W_i$. A valid beat causes the detector 88 to produce a 1 output on line 92 leading to a multiplier function 94. If the current beat is not valid, a "zero" is applied to the multiplier, effectively eliminating the current beat value from being applied to the summing circuit 96 forming a part of the ensemble averaging operation. The detector 88, itself, determines the degree of similarity between the present windowed heart sound and the immediately preceding windowed heart sound and if they match in a predetermined respect as determined by total squared error as above or cross-correlation, the current beat will be considered valid and will be used to update the ensemble. Summation 96 and delay 98 operate together to produce a vector ensemble average of $\vec{W}$ over an interval of roughly 8 heart beats. The interval $\alpha t$ is determined by $\alpha 2=\frac{7}{8}$. the delay 98 may be implemented as a register with a clock enable. If the "detect" output from detector 88 is "1", then the current input $\vec{W}_i$ is used to update the ensemble Vector $\vec{Ens}_i$.

Figure 3C:
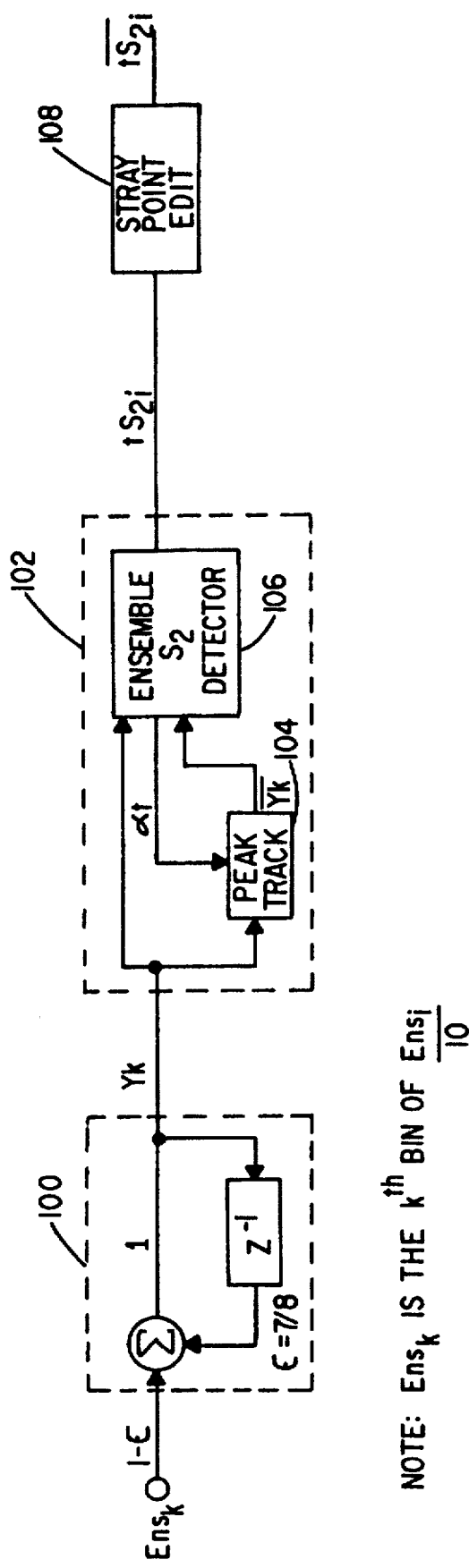

Referring next to FIG. 3C, an explanation will now be provided of the peak detection processing steps employed to locate the peak value of the ensemble averaged heart sound envelope so that the $S_2$ time interval is established.

The vector of the ensemble averaged heart sound envelope $Ens_i$ is first smoothed by being treated as a waveform which is exponentially filtered with a low pass filter shown enclosed dashed line box 100. The filtering tends to smooth any rough edges that may exist in that waveform. Thus, the signal $Y_k$ shown in FIG. 3C represents the smoothed ensemble averaged heart sound envelope. This signal train is applied to the ensemble $S_2$ detection operations shown enclosed by solid line box 102.

The detection of the time $S_2$ relative to the "R-wave" for each beat is calculated by subtracting the time of the "R-wave" from the time of $S_2$. The detection rule employed is similar to mathematically detecting a peak in a waveform, but with some added considerations. First off, there is usually more than one peak in the ensemble buffer. Further, the correct peak is not always the first one nor is the highest peak always the correct peak. The following detection rule was heuristically determined after numerous hours of manually marking intermediate detector outputs and comparing them with known correct answers.

In order for a peak to be selected, it must pass two tests in sequence before the occurrence of the next local maximum. The first peak to pass both of the tests described below is selected as $S_2$. As soon as the smoothed ensemble reaches a local maximum, the peak tracker 104 holds the peak value $Y_k$ for prescribed time defined below.

With reference to FIG. 7, the smoothed ensemble must fall by a minimum of $\Delta Y_1$ from a most recent local peak within a minimum time interval $\Delta X_{min}$ to qualify the most recent local maximum as a candidate peak. This requirement allows the detector 106 to ignore abnormally narrow transitions or noise.

Passing the first test marks the time where the peak tracker must begin timing an extended hold of $Y_p$ for an additional $\Delta X_2$ counts. This is necessary because $Y_p$ is also used in the next test, but the tracker 104 will hold only an additional $\Delta X_{min}+\Delta X_2$ to avoid skipping over the next peak. The extended hold is referenced to the passing of the first test rather than the actual peak location, because occasionally a valid peak can be expectedly wide.

The second test which is then applied to detect the time of $S_2$ is that the smoothed ensemble must fall by a minimum of $\Delta Y_2$ from the most recent local $Y_p$ before the tracker output $Y_p$ glides into the next smoothed ensemble peak to confirm the most recent local maximum as the true $S_2$ peak. If the $Y_k$ value and the smooth ensemble collide before the second test is passed, the current peak is discarded and the next peak is examined.

One final step is preferably executed before reporting the expected time of the heart sound $S_2$ for a given beat. The ensemble detection stream is compared to an exponentially filtered version of validated measurements. A measurement is considered valid in the detection stream for $S_2$ if it is ±15% of the running estimate. Valid measurements are used to update running estimates. Where a measurement deviates from the running estimate by more than 15%, it is eliminated by the stray point edit operation represented by block 108 in FIG. 3c.

The output from the "stray point edit" at circuit 108 in FIG. 3c comprises a number of counts beginning with the R-wave and ending with the location of the extracted peak value for $S_2$, as determined by the operation represented by block 102.

While the invention has been described in connection with determining the $S_2$ interval, by appropriately selecting the upper and lower cut-off frequencies for the bandpass filter 46 and the cut-off frequency for the low-pass filter 80 and the window rules for the $GET_w$ operation 84, one can isolate heart sound $S_1$ as well. Knowing both $S_1$ and $S_2$, the heart's left ventricular ejection time can be determined. With further reference to FIG. 1, it is also possible to derive the heart's pre-ejection period, a parameter that has been used in the past to control rate adaptive pacers. Those skilled in the art may recognize other advantages to be gained in diagnosis and therapy delivery from information obtained from an implanted accelerometer when employing the signal processing capabilities afforded by the present invention.

This invention has been described herein in considerable detail in order to comply with the Patent Statutes and to provide those skilled in the art with the information needed to apply the novel principles and to construct and use such specialized components as are required. However, it is to be understood that the invention can be carried out by specifically different equipment and devices, and that various modifications, both as to the equipment details and operating procedures, can be accomplished without departing from the scope of the invention itself.

What is claimed is:

1. Cardiac stimulating apparatus, comprising:

pulse generator means for producing cardiac stimulating pulses at predetermined times;

means for sensing R-wave events;

accelerometer means for sensing movement of body structures of a patient, said accelerometer means producing an analog electrical output signal proportional to such movement;

signal processing means coupled to receive the analog electrical output signals and signals corresponding to R-wave events for isolating in said analog electrical output signal components corresponding to a predetermined heart sound in relation to a time of occurrence of said R-wave events; and means responsive to the length of an interval between the occurrence of R-wave events and a next occurring predetermined heart sound for controlling the time that the pulse generator means produces cardiac stimulating pulses.

2. The apparatus as in claim 1 wherein the signal processing means includes:

pre-processing means coupled to receive the analog electrical output signal of the accelerometer means for producing therefrom a log normalized heart sound envelope signal.

3. The apparatus as in claim 2 wherein the pre-processing means includes:

bandpass filter means having an upper and a lower cut-off frequency defining a pass-band for filtering out components in the analog output signal due to at least one of breathing, body motion, muscle twitch and voice.

4. The apparatus as in claim 3 wherein the pre-processing means further includes:

automatic gain control means coupled to said bandpass filter means for removing any transient spikes in the analog electrical output signal whose amplitude exceeds a predetermined threshold and whose time constant is less than a predetermined value.

5. The apparatus as in claim 4 wherein the preprocessing means further includes:

means coupled to the automatic gain control means for low-pass filtering and absolute value of an output from said bandpass filter means for producing a heart sound envelope signal; and means coupled to receive the heart sound envelope signal for logarhythmically compressing said heart sound envelope signal.

6. The apparatus as in claim 2 and further including:

means for establishing a time window beginning and ending at predetermined times following the given R-wave event where the beginning and ending times are a function of a detected R-to-R interval, the means for establishing a time window capturing only a portion of the log normalized heart sound envelope signal falling within said time window.

7. The apparatus as in claim 6 wherein the window's beginning and ending times straddle an expected time of occurrence of the predetermined heart sound.

8. The apparatus as in claim 7 wherein the predetermined heart sound comprises heart sound $S_2$.

9. The apparatus as in claim 7 wherein the predetermined beginning and ending times are expressed as:

$S_b = 119.0 - 0.625(HR - 120)$ in counts at a 500 ms sample rate for all heart rates (HR) and $S_e = 198.0 - 2.0875(HR - 120)$ in counts at 500 ms sample rate where HR<120 bpm and $S_e = 198.0 - 1.225(HR - 120)$ in counts at 500 ms sample rate where HR>120 bpm.

10. The apparatus as in claim 6 and further including means for comparing the portion of the log normalized heart sound envelope captured by the means for establishing a time window during a current R-to-R interval with the portion of the log normalized heart sound envelope captured by the means for establishing a time window during a preceding R—R interval for morphologic similarity; and means for computing an ensemble average of only the captured portion of the log normalized heart sound envelope captured during the current R-to-R interval that is morphologically similar to the portion of the log normalized heart sound envelope captured during the preceding R-to-R interval; and means for storing a computed result.

11. The apparatus as in claim 10 and further including means for calculating a time interval between a predetermined peak in the stored computed result and a preceding R-wave event.

12. In an implantable, rate-adaptive cardiac pacer of the type comprising R-wave sensing means, ventricular pacing means, an accelerometer-based activity sensing means for producing analog electrical output signal corresponding to movement of body structures, and a microprocessor-based controller coupled to the R-wave sensing means, the ventricular pacing means and the accelerometer-based activity sensing means for controlling the operation of the ventricular pacing means to issue ventricular pacing pulses at a rate determined by the activity sensing means, apparatus for establishing a hemodynamic upper rate limit for the ventricular pacing means, comprising:

signal processing means including the microprocessor-based controller for deriving from the analog electrical output signals a time interval between a detection of an R-wave event by the R-wave sensing means and an ensuing heart sound;

means for producing a control signal proportional to said time interval; and means responsive to said control signal for setting said upper rate limit.

13. The cardiac pacer as in claim 12 wherein the microprocessor-based controller includes:

memory means for storing a fixed parameter corresponding to a time interval between heart sound, $S_2$, and heart sound, $S_3$, measured when a patient in whom the pacer is implanted is inactive; and means for adding said fixed parameter to said time interval between a detection of an R-wave event by the R-wave sensing means and the ensuing heart sound, said control signal being proportional to a sum thereof.

14. The cardiac pacer as in claim 13 wherein the signal processing means includes:

pre-processing means coupled to receive the analog electrical output signals from the accelerometer means for producing therefrom a log normalized heart sound envelope signal.

15. The apparatus as in claim 14 wherein the preprocessing means includes:

bandpass filter means having an upper and a lower cut-off frequency defining a pass-band for eliminating components in the analog output signal due to breathing, body motion, muscle twitch and voice.

16. The cardiac pacer as in claim 15 wherein the preprocessing means further includes automatic gain control means coupled to the bandpass filter means for removing any transient spikes in the analog electrical output signal whose amplitude exceeds a predetermined threshold and whose time constraint is less than a predetermined value.

17. The cardiac pacer as in claim 16 wherein the preprocessing means further includes:

means coupled to the automatic gain control means for low-pass filtering an absolute value of an output from the bandpass filter means for producing a heart sound envelope signal; and means coupled to receive the heart sound envelope signal for logarhythmically compressing said heart sound envelope.

18. The cardiac pacer as in claim 14 and further including means for establishing a time window beginning and ending at predetermined times following a given R-wave signal where the beginning and ending times are a function of a detected R-to-R interval;

the means for establishing a time window capturing only a portion of the log normalized heart sound envelope falling within said time window.

19. A cardiac pacer as in claim 18 and further including:

means for comparing the portion of the log normalized heart sound envelope captured by the means for establishing a time window during a current R-to-R interval with the portion of the log normalized heart sound envelope captured by the means for establishing a time window during a preceding R-to-R interval for morphologic similarity; and means for computing an ensemble average of only the captured portion of the log normalized heart sound envelope captured during the current R-to-R interval that is morphologically similar to the portion of the log normalized heart sound envelope captured during the preceding R-to-R interval and storing a computed result.

20. The cardiac pacer as in claim 19 and further including:

means for calculating a time interval between a predetermined peak in the stored computed result and a preceding R-wave.

* * * * *